(12) United States Patent
Zierhofer (10) Patent No.: US 8,023,586 B2
(45) Date of Patent: Sep. 20, 2011

(54) INDUCTIVE POWER AND DATA TRANSMISSION SYSTEM BASED ON CLASS D AND AMPLITUDE SHIFT KEYING

(75) Inventor: Clemens M. Zierhofer, Kundl (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1142 days.

(21) Appl. No.: 11/675,176

(22) Filed: Feb. 15, 2007

(65) Prior Publication Data
US 2008/0198947 A1    Aug. 21, 2008

(51) Int. Cl.
*H04L 27/00*    (2006.01)
(52) U.S. Cl. ...................................... 375/295
(58) Field of Classification Search .......... 375/268, 375/295, 300, 301, 309, 320; 600/25
See application file for complete search history.

(56) References Cited

U.S. PATENT DOCUMENTS

| | | | |
|---|---|---|---|
| 4,284,856 A | 8/1981 | Hochmair et al. | 179/107 E |
| 4,357,497 A | 11/1982 | Hochmair et al. | 179/107 E |
| 4,428,377 A | 1/1984 | Zollner et al. | 128/419 R |
| 4,592,359 A | 6/1986 | Galbraith | 128/419 R |
| 4,689,819 A | 8/1987 | Killion | 381/68 |
| 5,069,210 A | 12/1991 | Jeutter et al. | 128/420.6 |
| 5,095,904 A | 3/1992 | Seligman et al. | 128/420.6 |
| 5,570,086 A | 10/1996 | Hanaoka et al. | 340/825.54 |
| 5,571,148 A | 11/1996 | Loeb et al. | 607/57 |
| 5,601,617 A | 2/1997 | Loeb et al. | 607/56 |
| 5,741,314 A | 4/1998 | Daly et al. | 607/60 |
| 5,749,912 A | 5/1998 | Zhang et al. | 607/57 |
| 6,031,862 A | 2/2000 | Fullerton et al. | 375/200 |
| 6,067,474 A | 5/2000 | Schulman et al. | 607/57 |
| 6,181,969 B1 | 1/2001 | Gord | 607/59 |
| 6,792,050 B1* | 9/2004 | Shiikuma et al. | 375/300 |
| 7,120,501 B2 | 10/2006 | Boylston et al. | 607/57 |
| 2004/0124915 A1* | 7/2004 | Heubi et al. | 330/10 |
| 2004/0184289 A1* | 9/2004 | Vinciarelli | 363/15 |
| 2005/0063488 A1 | 3/2005 | Troyk et al. | 375/316 |
| 2006/0264196 A1* | 11/2006 | Fan | 455/336 |

FOREIGN PATENT DOCUMENTS
WO    WO 2008/101151    8/2008

OTHER PUBLICATIONS

Galbraith, D., et al, "A Wide-Band Efficient Inductive Transdermal Power and Data Link with Coupling Insensitive Gain", *IEEE Transactions on Biomedical Engineering*, vol. BME-34, No. 4, Apr. 1987, pp. 265-275.
Gheewala, T. R., et al, "A CMOS Implantable Multielectrode Auditory Stimulator for the Deaf", *IEEE Journal of Solid-State Circuits*, 1975; pp. 472-479.
Loizou, Philipos C., "Introduction to Cochlear Implants", *IEEE Signal Processing Magazine*, Sep. 1998, pp. 101-130.

(Continued)

*Primary Examiner* — Sam K Ahn
(74) *Attorney, Agent, or Firm* — Sunstein Kann Murphy & Timbers LLP (57) ABSTRACT

A rf signal transfer link is described which uses amplitude shift keying (ASK) to transfer rf data pulses. The link minimizes state transition time at the end of each data pulse.

24 Claims, 5 Drawing Sheets

OTHER PUBLICATIONS

Thao, Nguyen T., et al, "Deterministic Analysis of Oversampled A/D Conversion and Decoding Improvement Based on Consistent Estimates", *IEEE Transactions on Signal Processing*, vol. 42, No. 3, Mar. 1994, pp. 519-531.

Zierhofer, Clemens, M., et al, "Electronic Desing of a Cochlear Implant for Multichannel High-Rate Pulsalile Stimulation Strategies", *IEEE Transactions on Rehabilitation Engineering*, vol. 3, No. 1, Mar. 1995, pp. 112-116.

Zierhofer, C.M., et al, "Geometric Approach for Coupling Enhancement of Magnetically Coupled Coils", *IEEE Transactions on Biomedical Engineering*, vol 43, No. 7, Jul. 1996, pp. 708-714.

Zierhofer, Clemens M., "Adaptive Sigma-Delta Modulation with One-Bit Quantization", *IEEE Transactions on Circuits and Systems,—II Analog and Digital Signal Processing*, vol. 47, No. 5, May 2000, pp. 408-415.

Zierhofer, C.M., et al, "High-Efficiency Coupling-Insensitive Transcutaneous Power and Data Transmission Via an Inductive Link", *IEEE Transactions on Biomedical Engineering*, vol. 37, No. 7, Jul. 1990, pp. 716-722.

Hintea et al., "Radio Frequency Link Used in Partially-Implanted Auditory Prosthesis", Electronics, Circuits, and Systems, 1996, ICECS '96, vol. 2, pp. 1143-1146.

International Searching Authority, International Search Report—International Application No. PCT/US2008/054065, dated Aug. 18, 2008, together with the Written Opinion of the International Searching Authority, 9 pages.

\* cited by examiner

INDUCTIVE POWER AND DATA TRANSMISSION SYSTEM BASED ON CLASS D AND AMPLITUDE SHIFT KEYING

FIELD OF THE INVENTION

The present invention relates to signal processing, and specifically, to providing data power signals to implanted systems.

BACKGROUND ART

One way to provide power and data to an implanted electronic system such as a prosthetic stimulator is to transmit an RF signal via an inductive link. An inductive link basically has two resonant circuits: an external one and an internal one implanted in the patient user. The inductances of the two resonant circuits are realized, for example, as two spiral-shaped coils with typical outer diameters between 20 and 30 mm. When facing each other, the coils form a transformer which allows the transfer of RF-energy. Inductive links have been investigated with respect to optimizing power transfer efficiency and coupling misalignment tolerance. See, e.g., Galbraith D C, Soma M, and White R L, *A Wide-Band Efficient Inductive Transdermal Power And Data Link With Coupling Insensitive Gain*, IEEE Trans. Biomed. Eng. BME-34, pp. 265-275, April 1987; and Zierhofer C M and Hochmair E S, *High-Efficiency Coupling-Insensitive Power And Data Transmission Via An Inductive Link*, IEEE-Trans. Biomed. Eng. BME-37, pp. 716-723, July 1990; which are incorporated herein by reference.

Figure 1:
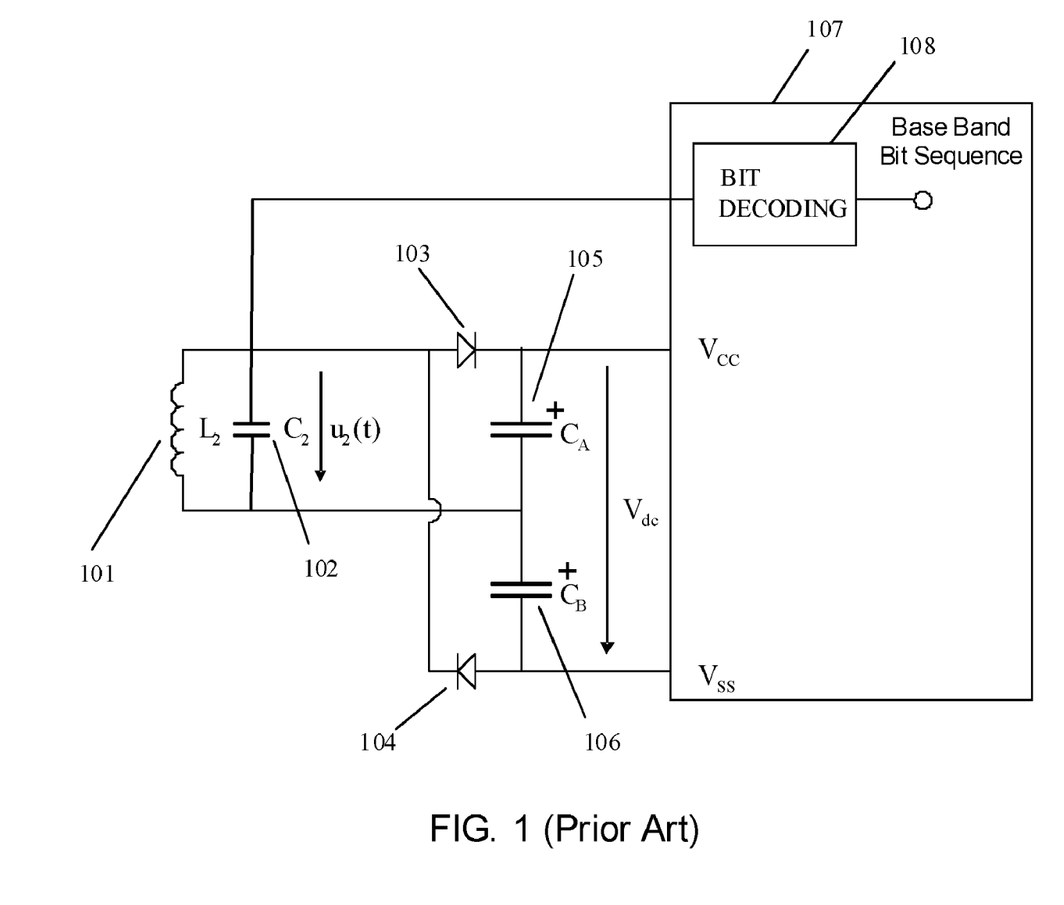
FIG. 1 shows a parallel tuned receiver resonant circuit and power supply voltage generation according to the prior art.

In many applications, parallel-tuned receiver circuits are used because the RF-voltage across the resonant circuit can easily be converted to a dc voltage by rectification and smoothing. The dc voltage then is used as a power supply voltage for the electronic circuits within the implanted system. For example, FIG. 1 shows a parallel-tuned receiver resonant circuit of coil 101 and capacitor 102 where signal $u_2(t)$ is the induced RF-voltage. Rectifier diodes 103 and 104 in combination with filtering capacitors 105 and 106 convert the ac voltage $u_2(t)$ to a dc-like voltage $V_{dc}$. If the filtering capacitors 105 and 106 are sufficiently large, any ac components of $V_{dc}$ can be neglected. Voltage $V_{dc}$ is connected to voltage supply ports $V_{CC}$ and $V_{SS}$ of a subsequent electronic circuit 107 which implements the functionality of the implanted system, e.g., an implanted prosthetic stimulator.

Signal $u_2(t)$ is not only used as supply voltage generation for power, but it also contains digital information data. For example, for a cochlear implant, signal $u_2(t)$ provides information defining short biphasic pulses for the electrical stimulation of the acoustic nerve. In general, a bit decoding stage 108 is part of an implanted system that converts the RF-signal $u_2(t)$ to a base band bit sequence used for further processing.

For digital data transfer, at least two different distinguishable states of $u_2(t)$ are defined. For example, these two different states could be two different operating frequencies of $u_2(t)$, which are in the vicinity of the resonance frequency $f_2$. Such a scheme is usually designated as Frequency-Shift-Keying (FSK). A practical example is described, e.g., in Galbraith above, where $f_2$=20 MHz, and the two operating frequencies are 19 MHz and 21 MHz.

Another way to encode digital information in signal $u_2(t)$ is with Amplitude Shift Keying (ASK). In an ASK-scheme, the two distinguishable states of $u_2(t)$ can qualitatively be described by "RF-amplitude present" and "no RF-amplitude present". These two (ideal) states can easily be detected by means of envelope detection. For example, in FIG. 1 decoding stage 108 would then include an envelope detector.

Figure 2:
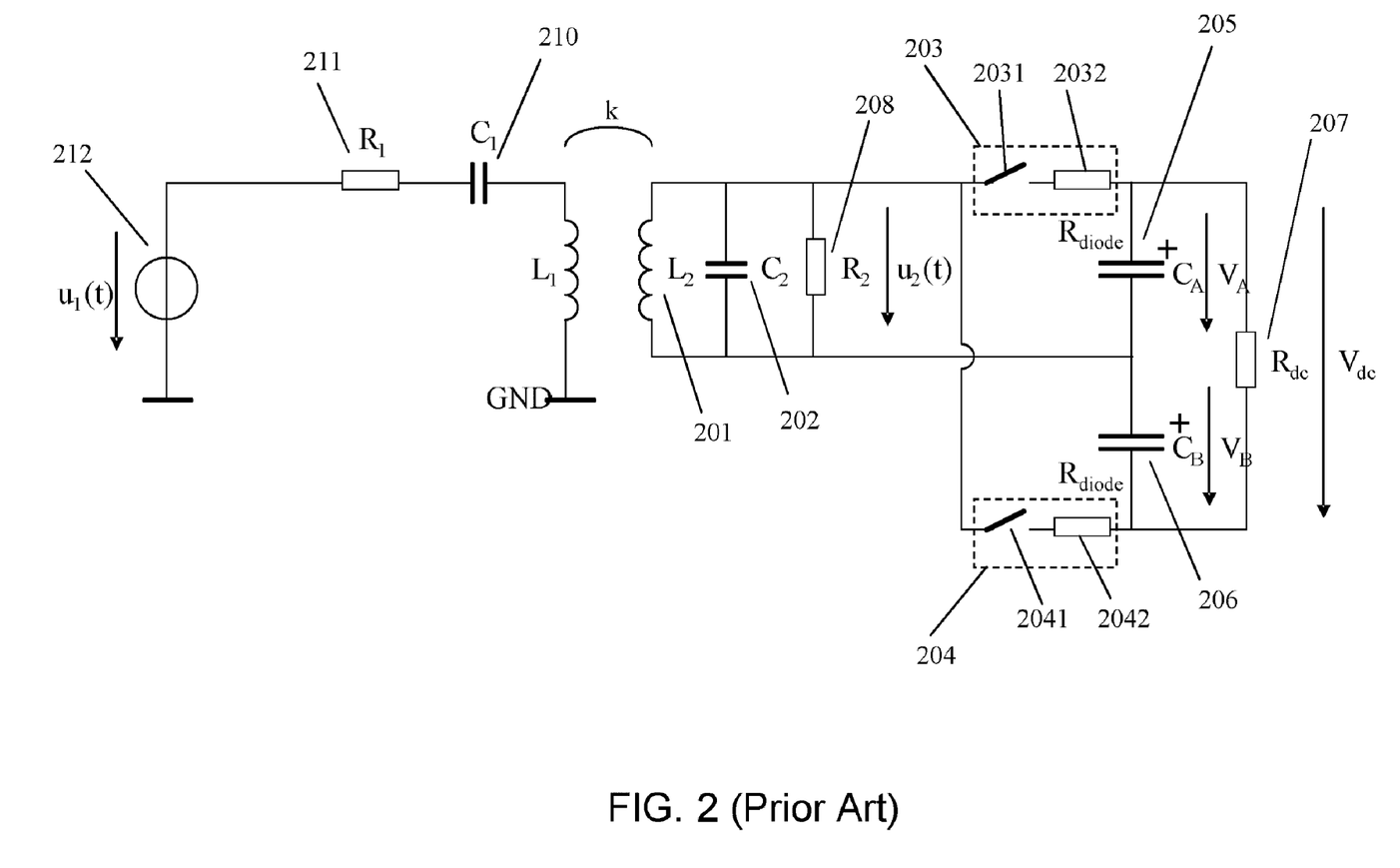
FIG. 2 shows an equivalent circuit of an inductive link with series-tuned transmitter and parallel-tuned receiver resonant circuit according to the prior art.

In FIG. 2, an equivalent circuit of an inductive link system is shown. The parallel-tuned receiver circuit includes receiver coil 201, capacitor 202, and resistor 208, where resistor 208 represents the ohmic losses due to the parasitic resistance of coil 201. Resonance frequency $f_2$ and unloaded quality factor $Q_{2,unloaded}$ are defined as $$f_2 = \frac{1}{2\pi\sqrt{L_2 C_2}}, \text{ and,} \quad (1)$$

$$Q_{2,unloaded} = R_2 \sqrt{\frac{C_2}{L_2}}. \quad (2)$$

The power consumption of stage 107 in FIG. 1 is represented by an ohmic load 207. Rectifier diodes 103 and 104 are represented by simple equivalent circuits 203 and 204, which themselves are composed of ideal switches 2031 and 2041, and ohmic resistors 2032 and 2042. The states of the switches depend on voltage $u_2(t)$ and voltages $V_A$ and $V_B$ across capacitors 205 and 206, respectively. It is assumed that switch 2031 is closed if $u_2(t) > V_A$, and it is in its high impedance state for $U_2(t) \leq V_A$. Similarly, switch 2041 is closed if $u_2(t) < -V_B$, and opened for $u_2(t) \geq -V_B$.

Receiver coil 201 is inductively coupled to a transmitter coil 209, and the coupling strength is described by coupling coefficient k. Transmitter coil 209 together with capacitor 210 and resistor 211 form a series-tuned transmitter resonance circuit, where resistor 211 represents the parasitic resistance of coil 209. Resonance frequency $f_1$ and unloaded quality factor $Q_{1,unloaded}$ are defined as:

$$f_1 = \frac{1}{2\pi\sqrt{L_1 C_1}}, \text{ and,} \quad (3)$$

$$Q_{1,unloaded} = \frac{\sqrt{\frac{L_1}{C_1}}}{R_1}. \quad (4)$$

Figure 3:
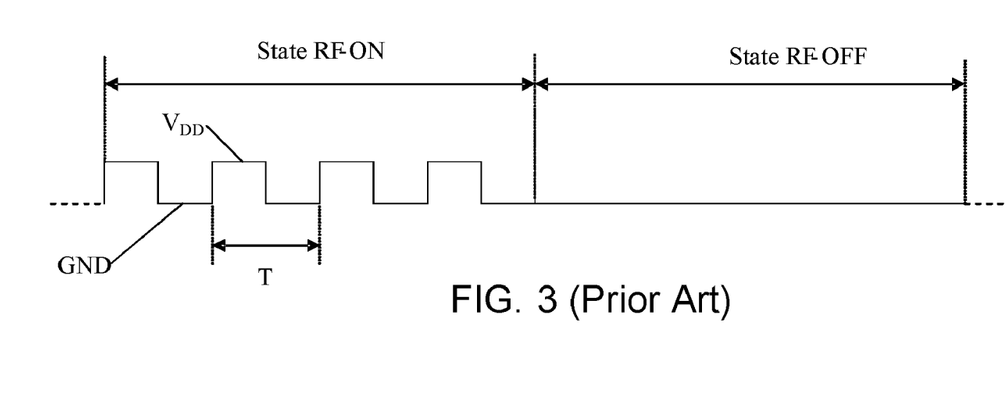
FIG. 3 shows modes of RF-ON and RF-OFF of input voltage $u_1(t)$ for Amplitude Shift Keying (ASK).

The input of the transmitter circuit is driven by voltage source 212 which generates input voltage $u_1(t)$. For ASK, typically two modes of operation, i.e., states RF-ON and RF-OFF, are used. As depicted in FIG. 3, in state RF-ON, $u_1(t)$ is switched periodically between ground potential and a supply voltage $V_{DD}$. Period T denotes the RF-period. During state RF-OFF, $u_1(t)$ is connected to ground potential.

Figure 4:
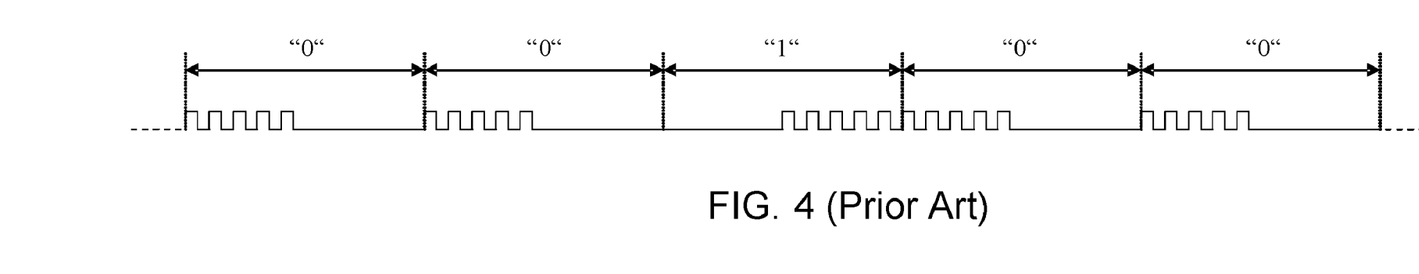
FIG. 4 shows an example of $u_1(t)$ for a bit sequence using a self clocking bit format.

FIG. 4 shows an example of voltage $u_1(t)$ for a sequence of bits using a self clocking bit format. Here, a logical "0" is encoded into a sequence RF-ON followed by RF-OFF, and vice versa, a logical "1" is encoded into a sequence RF-OFF followed by RF-ON.

SUMMARY OF THE INVENTION

Embodiments of the present invention are directed to an rf signal transfer link which uses amplitude shift keying (ASK) to transfer rf data pulses. The link includes means for minimizing state transition times.

For example, the means for minimizing may include means for changing a resonant circuit quality factor as would be useful in a parallel-tuned receiver circuit for receiving the rf data pulses or a series-tuned resonant transmitting circuit for transmitting the rf data pulses. For example, a series-tuned resonant transmitting circuit includes a class D amplifier driver. In a more specific embodiment, the class D amplifier may be integrated onto a single microchip. The series-tuned resonant transmitting circuit may include a damping resistor $R_D$ in series with a transmitter circuit inductance during the rf off time. For example, the damping resistor $R_D$ may be an open circuit with infinite resistance, or it may have an optimal resistance to minimize the state transition times. In some embodiments, the damping resistor $R_D$ may cause the resonant receiving circuit to behave such that rf waveform decay is independent of coupling factor.

Embodiments also include a receiver circuit for an implanted electronic system. An implanted receiver circuit receives amplitude shift keyed (ASK) rf data pulses from an external transmitter. The receiver circuit includes means for minimizing state transition times. In some embodiments, the means for minimizing may include means for changing a resonant circuit quality factor.

Embodiments also include a transmitter circuit for an implanted electronic system. An external transmitter circuit transmits amplitude shift keyed (ASK) rf data pulses to an implanted receiver. The transmitter circuit includes means for minimizing state transition times. The means for minimizing may include means for changing a resonant circuit quality factor, such as a series-tuned resonant transmitting circuit for transmitting the rf data pulses. The series-tuned resonant transmitting circuit may include a class D amplifier driver. In a more specific embodiment, the class D amplifier may be integrated onto a single microchip. The series-tuned resonant transmitting circuit may include a damping resistor $R_D$ in series with a transmitter circuit inductance during the rf off time. For example, the damping resistor $R_D$ may be an open circuit with infinite resistance, or it may have an optimal resistance to minimize receiving circuit state transition times. In some embodiments, the damping resistor $R_D$ may cause the resonant receiving circuit to behave such that rf waveform decay is independent of coupling factor.

Embodiments of the present invention also include an rf transfer link which uses amplitude shift keying (ASK) to transfer rf data pulses. The link includes means for causing the system to behave such that rf waveform decay is independent of coupling factor.

DETAILED DESCRIPTION OF SPECIFIC EMBODIMENTS

An ASK-based signal transfer link system for data and energy transmission as in FIG. 2 has a potential problem. Assuming a periodic sequence of input states RF-ON and RF-OFF of voltage $u_1(t)$, and also assuming steady state conditions, dc-voltage $V_{dc}$ across load $R_{dc}$ is constant. During state RF-ON, voltage $u_2(t)$ reaches a peak amplitude which is slightly higher than $V_{dc}/2$. Switches 2031 or 2041 are closed if $u_2(t)>V_{dc}/2$, or if $u_2(t)<-V_{dc}/2$ respectively. Only during these very short periods charge is flowing into the network $C_A, C_B, R_{dc}$. However, these diode currents define a particular loaded quality factor $Q_{2,loaded}$, which is considerably smaller than the unloaded quality factor $Q_{2,unloaded}$ as defined in Equation (2) above.

If $u_1(t)$ changes from state RF-ON to RF-OFF, the voltage amplitude of $u_2(t)$ cannot immediately follow such a change. Instead, it will take some time for the RF amplitude to decrease back towards baseline, and the velocity of decay is strongly influenced by the quality factor of the receiver circuit: the lower the quality factor, the faster the decay is. Unfortunately, basically the unloaded quality factor $Q_{2,unloaded}$ which is much higher than the loaded quality factor $Q_{2,loaded}$ applies here because as soon as the amplitude of $u_2(t)$ falls below $V_{dc}/2$, diode switches 2031 and 2041 remain open, and no RF energy can flow into the network $C_A, C_B, R_{dc}$. During RF-OFF, the only effective ac-load within the receiver circuit is $R_2$.

The exact relaxation behavior of $u_2(t)$ during RF-OFF is determined by the network $R_1, C_1, L_1, R_2, C_2, L_2$, and coupling factor k, and thus the unloaded quality factors $Q_{1,unloaded}$ and $Q_{2,unloaded}$ are relevant. However, these quality factors should be as high as possible with respect to a high power transfer efficiency during RF-ON. So the requirements for high power efficiency and fast RF-relaxation during RF-OFF in an ASK scheme are contradicting each other.

Figure 5:
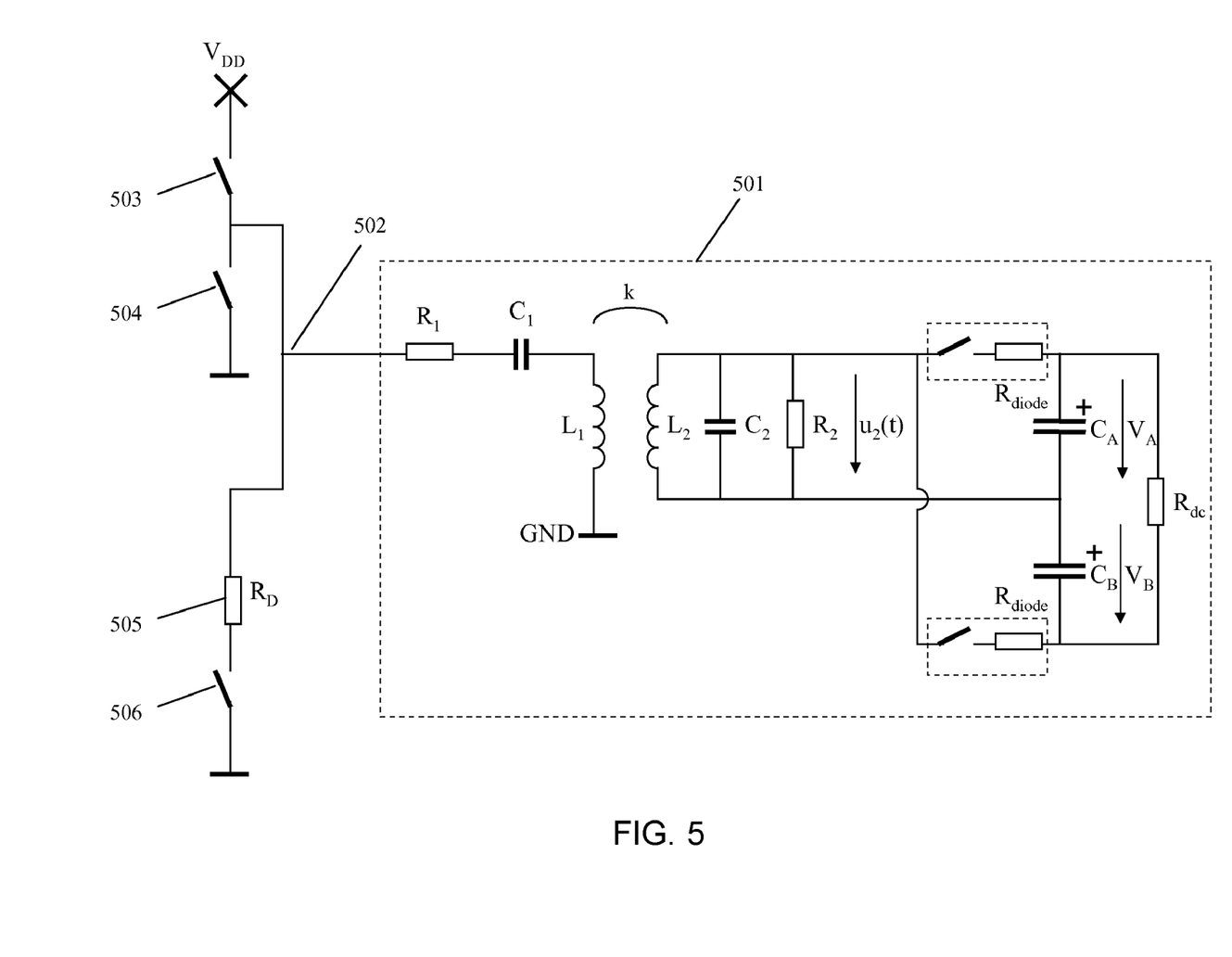
FIG. 5 shows an equivalent circuit of an inductive link with series-tuned transmitter and parallel-tuned receiver resonant circuit according to one embodiment of the present invention.

One way to address this problem is to decrease the quality factor in the transmitter resonant circuit during RF-OFF so that each rf data pulse will end with a more rapid decrease in pulse amplitude. One specific embodiment of a signal transfer link is shown in FIG. 5, which is a system for amplitude shift keying (ASK) transfer of rf data pulses. Block 501 represents the inductive signal transfer link. Block 501 includes an external series-tuned resonant transmitter circuit for transmitting the rf data pulses using ASK, and an implanted parallel-tuned receiver module for receiving the rf data pulses. The input node 502 is connected to a network composed of a switching pair 503 and 504, resistor 505 and switch 506. During state RF-ON, switch 506 is open (high impedance), and node 502 is switched between ground potential and supply voltage $V_{DD}$ by means of switching pair 503 and 504. This causes a rectangular voltage at radio frequency, and such an operating mode is usually designated as a class D switching paradigm. During state RF-OFF, switches 503 and 504 are open, and switch 506 is closed. Now $R_D$ series damping resistor 505 is connected to $R_1$ in series, which means a considerable reduction of the transmitter quality factor. This reduction of the quality factor for the transmitter resonant circuit at the end of each rf data pulse accelerates the decay of the RF amplitude in the receiver resonant circuit so as to minimize the time required for the trailing edge of the pulse to rapidly decrease back to baseline.

Figure 6:
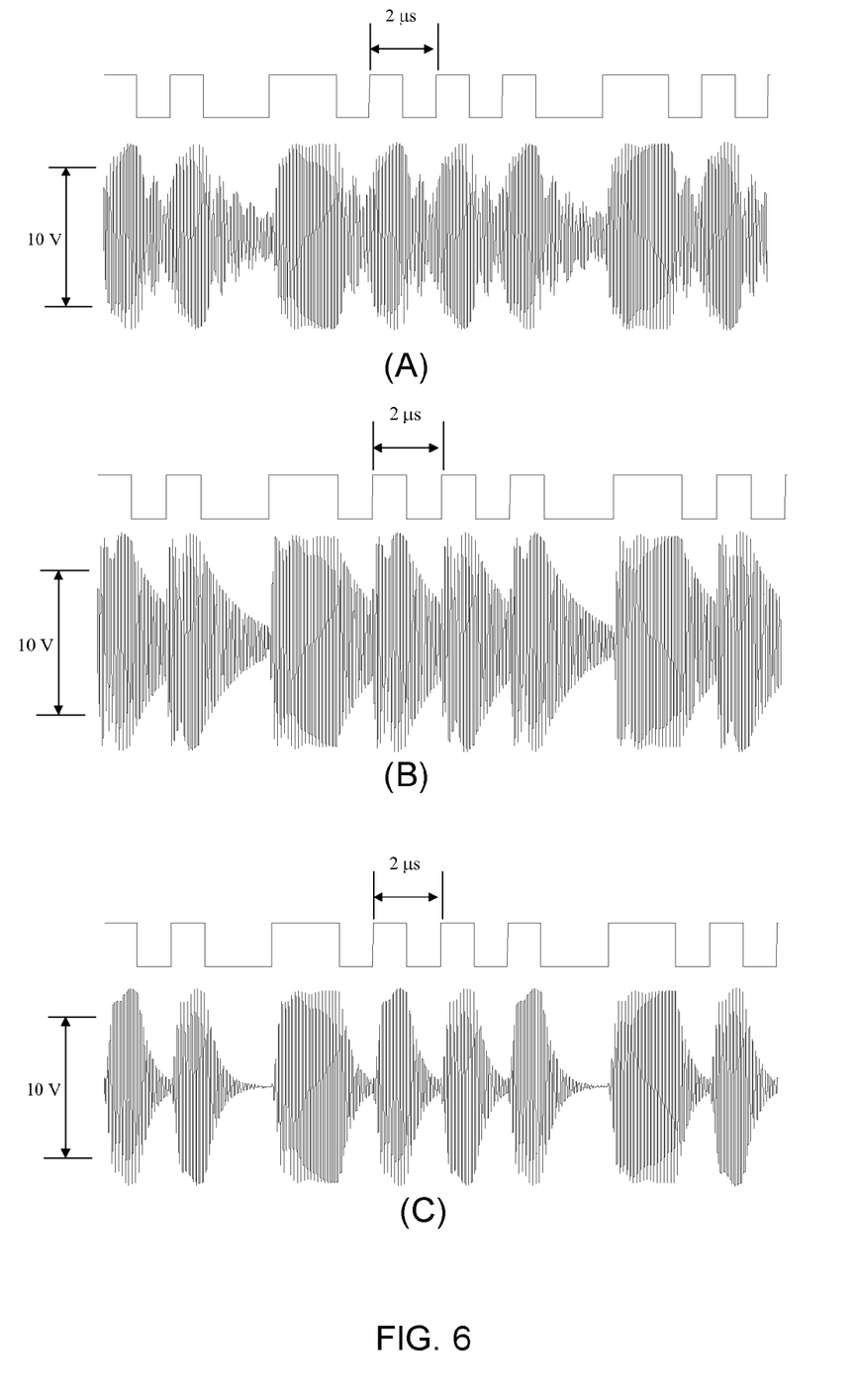
FIG. 6A-C shows state signals and voltage traces for various circuit values in a receiver resonant circuit.

A quantitative analysis for the circuit in FIG. 5 has been carried out with specifications as summarized in Table 1. The simulations are based on a state space model with a computation time increment of 0.5 ns. The RF frequency is 10 MHz, resulting in T=100 ns. Simulation results are shown in FIG. 6A-C where the upper traces depict signal state. For STATE=HIGH, the class D driver produces an RF-signal (state RF-ON), and for STATE=LOW, the input of the transmitter series circuit is connected to $R_D$ (state RF-OFF). Here, a self-clocking bit format with bit duration of 2 µs is assumed.

Note that the shortest possible duration for RF-ON is 1 μs, which contains exactly 10 RF cycles.

TABLE 1

Circuit Specifications

| | |
|---|---|
| k | 0.2 |
| $V_{DD}$ | 3 V |
| $L_1$ | 2.70 μH |
| $L_2$ | 0.85 μH |
| $C_1$ | 82 pF |
| $C_2$ | 260 pF |
| $C_A$ | 10 nF |
| $C_B$ | 10 nF |
| $R_1$ | 2 Ω |
| $R_2$ | 2100 Ω |
| $R_{diode}$ | 40 Ω |
| $R_{dc}$ | 10 kΩ |

Further simulations have been computed for different values of $R_D$ at a coupling of k=0.2. FIG. 6A shows the result for $R_D$=0. Obviously, during periods STATE=0, the amplitude of $u_2(t)$ is decaying quite slowly and the decay is superimposed by a typical beat effect. Energy is oscillating between the transmitter and receiver resonant circuits with a beat frequency of about 2 MHz. Although the data structure can be identified visually, data detection by means of an electronic circuit cannot be easily achieved.

If the damping resistor is set to $R_D \rightarrow \infty$ as shown in FIG. 6B, the beat effect disappears. In this case, the receiver resonant circuit relaxes as if it was not coupled to the transmitter because the current in the transmitter is forced to zero. Thus the behavior of a 2nd order system is observed, i.e., the amplitude of $u_2(t)$ decays exponentially according to the time constant of the unloaded receiver circuit $L_2$, $C_2$, $R_2$. The waveform $u_2(t)$ here is less complex as compared to FIG. 6A. Note that the decay for $R_D \rightarrow \infty$ is independent of coupling factor k, which might be an important feature for subsequent data decoding stages. For example, in a cochlear implant system this is an important criterion because the data decoding should be insensitive the mutual coil positions.

FIG. 6C shows the case for $R_D$=150Ω. Voltage $u_2(t)$ clearly outperforms FIGS. 6A and 6B, decaying comparatively fast at the end of each rf data pulse. Thus $u_2(t)$ is very well suited for data decoding.

One intrinsic advantage of embodiments such as the one shown in FIG. 5 is that many components of the external system can be integrated onto a single microchip, and thus power consumption and system size can be kept very small. Also, an rf generator (not shown in FIG. 5) to drive switches 503 and 504 during RF-ON can easily be integrated onto such a microchip. The performance of switches 503 and 504 is of particular importance: the ON-resistances typically should not exceed 1Ω, and the gate capacitances should be smaller than 10 pF. However, such characteristics can be achieved with existing technologies such as, e.g., 0.35 μm CMOS. In many signal transfer link applications, it may also be important that switches 503 and 504 are not closed simultaneously during RF-ON. Otherwise, very large currents can flow through the switches which dramatically enhance the power consumption and may damage circuit components.

Although various exemplary embodiments of the invention have been disclosed, it should be apparent to those skilled in the art that various changes and modifications can be made which will achieve some of the advantages of the invention without departing from the true scope of the invention.

What is claimed is:

1. An rf (radio frequency) signal transfer link comprising: a signal transfer link for using amplitude shift keying (ASK) to transfer rf data pulses, the link including a receiver circuit and a transmitter circuit, the transmitter circuit having an rf ON state and an rf OFF state, the transmitter circuit reducing the resonant circuit quality factor of the transmitter circuit during said rf OFF state, relative to the resonant circuit quality factor of the transmitter circuit during said rf ON state, thereby accelerating decay of rf amplitude at the receiver circuit during said rf Off state.

2. A link according to claim 1, wherein the receiver circuit includes a parallel-tuned receiver circuit for receiving the rf data pulses.

3. A link according to claim 1, wherein the transmitter includes a series-tuned resonant transmitting circuit for transmitting the rf data pulses.

4. A link according to claim 3, wherein the series-tuned resonant transmitting circuit includes a class D amplifier driver.

5. A link according to claim 4, wherein the class D amplifier is integrated onto a single microchip.

6. A link according to claim 3, wherein the series-tuned resonant transmitting circuit includes a damping resistor $R_D$ in series with a transmitter circuit inductance during the rf off time.

7. A link according to claim 6, wherein the damping resistor $R_D$ is an open circuit with infinite resistance.

8. A link according to claim 6, wherein the damping resistor $R_D$ has an optimal resistance to minimize receiver circuit state transition times.

9. A link according to claim 6, wherein the damping resistor $R_D$ has a resistance which causes the resonant receiving circuit to behave such that rf waveform decay is independent of coupling factor.

10. A transmitter circuit for an implanted electronic system, the circuit comprising:
an external transmitter circuit for transmitting amplitude shift keyed (ASK) rf (radio frequency) data pulses to an implanted receiver, the transmitter circuit having an rf ON state and an rf OFF state, the transmitter circuit reducing the resonant circuit quality factor of the transmitter circuit during said rf OFF state, relative to the resonant circuit quality factor of the transmitter circuit during said rf ON state, thereby accelerating decay of rf amplitude at the implanted receiver during said rf Off state.

11. A transmitter circuit according to claim 10, wherein the external transmitter circuit includes a series-tuned resonant transmitting circuit for transmitting the rf data pulses.

12. A transmitter circuit according to claim 11, wherein the series-tuned resonant transmitting circuit includes a class D amplifier driver.

13. A transmitter circuit according to claim 12, wherein the class D amplifier is integrated onto a single microchip.

14. A transmitter circuit according to claim 11, wherein the series-tuned resonant transmitting circuit includes a damping resistor $R_D$ in series with a transmitter circuit inductance during the rf off time.

15. A transmitter circuit according to claim 14, wherein the damping resistor $R_D$ is an open circuit with infinite resistance.

16. A transmitter circuit according to claim 14, wherein the damping resistor $R_D$ has an optimal resistance to minimize receiver circuit state transition times.

17. A transmitter circuit according to claim 14, wherein the damping resistor $R_D$ has a resistance which causes the resonant receiving circuit to behave such that rf waveform decay is independent of coupling factor.

18. An rf (radio frequency) transfer link comprising:
a signal transfer link for using amplitude shift keying (ASK) to transfer rf data pulses from a transmitter to a receiver, the transmitter having an rf ON state and an rf OFF state, the link reducing the resonant circuit quality factor of the transmitter during said rf OFF state, relative to the resonant circuit quality factor of the transmitter circuit during said rf ON state, such that rf waveform decay at the receiver is accelerated and independent of coupling factor.

19. An rf (radio frequency) signal transfer link comprising:
a signal transfer link for using amplitude shift keying (ASK) to transfer rf data pulses, the link including:
a series-tuned resonant transmitting circuit for transmitting the rf data pulses, the series-tuned resonant transmitter circuit having an rf ON state and an rf OFF state, the series-tuned resonant transmitting circuit including a damping resistor $R_D$ in series with a transmitter circuit inductance during said rf Off state,
wherein the damping resistor $R_D$ is an open circuit with infinite resistance to minimize state transition times.

20. An rf (radio frequency) signal transfer link comprising:
a signal transfer link for using amplitude shift keying (ASK) to transfer rf data pulses, the link including:
a series-tuned resonant transmitting circuit for transmitting the rf data pulses, the series-tuned resonant transmitter circuit having an rf ON state and an rf OFF state, the series-tuned resonant transmitting circuit including a damping resistor $R_D$ in series with a transmitter circuit inductance during said rf Off state,
wherein the damping resistor $R_D$ has an optimal resistance to minimize receiver circuit state transition times.

21. An rf (radio frequency) signal transfer link comprising:
a signal transfer link for using amplitude shift keying (ASK) to transfer rf data pulses, the link including:
a series-tuned resonant transmitting circuit for transmitting the rf data pulses, the series-tuned resonant transmitter circuit having an rf ON state and an rf OFF state, the series-tuned resonant transmitting circuit including a damping resistor $R_D$ in series with a transmitter circuit inductance during said rf Off state,
wherein the damping resistor $R_D$ has a resistance which causes the resonant receiving circuit to behave such that rf waveform decay is independent of coupling factor so as to minimize state transition times.

22. A transmitter circuit for an implanted electronic system, the circuit comprising:
an external transmitter circuit for transmitting amplitude shift keyed (ASK) rf (radio frequency) data pulses to an implanted receiver, the transmitter circuit having an rf ON state and an rf OFF state, the transmitter circuit including:
a series-tuned resonant transmitting circuit for transmitting the rf data pulses, the series-tuned resonant transmitting circuit including a damping resistor $R_D$ in series with a transmitter circuit inductance during said rf Off state,
wherein the damping resistor $R_D$ is an open circuit with infinite resistance to minimize state transition times.

23. A transmitter circuit for an implanted electronic system, the circuit comprising:
an external transmitter circuit for transmitting amplitude shift keyed (ASK) rf (radio frequency) data pulses to an implanted receiver, the transmitter circuit having an rf ON state and an rf OFF state, the transmitter circuit including:
a series-tuned resonant transmitting circuit for transmitting the rf data pulses, the series-tuned resonant transmitting circuit including a damping resistor $R_D$ in series with a transmitter circuit inductance during said rf Off state,
wherein the damping resistor $R_D$ has an optimal resistance to minimize receiver circuit state transition times.

24. A transmitter circuit for an implanted electronic system, the circuit comprising:
an external transmitter circuit for transmitting amplitude shift keyed (ASK) rf (radio frequency) data pulses to an implanted receiver, the transmitter circuit having an rf ON state and an rf OFF state, the transmitter circuit including:
a series-tuned resonant transmitting circuit for transmitting the rf data pulses, the series-tuned resonant transmitting circuit including a damping resistor $R_D$ in series with a transmitter circuit inductance during said rf Off state,
wherein the damping resistor $R_D$ has a resistance which causes the resonant receiving circuit to behave such that rf waveform decay is independent of coupling factor so as to minimize state transition times.

* * * * *